(12) United States Patent
Hamilton et al.

(10) Patent No.: US 8,921,590 B2
(45) Date of Patent: Dec. 30, 2014

(54) OLIGOMERISATION PROCESS

(75) Inventors: Paul Hamilton, Brussels (BE); John S. Godsmark, Antwerp (BE); David E. Heather, Hampshire (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 265 days.

(21) Appl. No.: 13/510,501

(22) PCT Filed: Nov. 23, 2010

(86) PCT No.: PCT/EP2010/067989
§ 371 (c)(1),
(2), (4) Date: Jul. 26, 2012

(87) PCT Pub. No.: WO2011/072992
PCT Pub. Date: Jun. 23, 2011

(65) Prior Publication Data
US 2012/0283465 A1 Nov. 8, 2012

(30) Foreign Application Priority Data
Dec. 15, 2009 (EP) .................... 09179262

(51) Int. Cl.
*C07C 67/303* (2006.01)
*C07C 29/04* (2006.01)
*C07C 2/04* (2006.01)
*B01J 29/40* (2006.01)
*B01J 29/70* (2006.01)
*B01J 29/80* (2006.01)
*B01J 29/90* (2006.01)
*B01J 35/00* (2006.01)
*C07C 2/12* (2006.01)
*C10G 50/00* (2006.01)
*C08F 110/06* (2006.01)
*C08F 210/16* (2006.01)

(52) U.S. Cl.
CPC .............. *B01J 29/40* (2013.01); *B01J 29/7026* (2013.01); *B01J 29/7042* (2013.01); *B01J 29/80* (2013.01); *B01J 29/90* (2013.01); *B01J 35/0006* (2013.01); *C07C 2/12* (2013.01); *C10G 50/00* (2013.01); *C08F 110/06* (2013.01); *C08F 210/16* (2013.01); *C10G 2300/4031* (2013.01); *C10G 2300/1088* (2013.01); *C10G 2400/20* (2013.01); *C10G 2400/22* (2013.01)
USPC ................ 560/1; 585/533; 585/501; 568/895

(58) Field of Classification Search
CPC ........ C07C 2/12; C07C 67/303; C07C 29/04; C07C 2/04; B01J 19/00; C10G 2300/4031; C10G 2300/1088
USPC ........................ 585/501, 533; 560/1; 895/568
See application file for complete search history.

(56) References Cited

U.S. PATENT DOCUMENTS

| 4,504,693 | A | 3/1985 | Tabak et al. |
| 4,544,788 | A | 10/1985 | Daviduk et al. |
| 5,472,670 | A | 12/1995 | Harrington et al. |
| 6,062,065 | A | 5/2000 | Sugimoto et al. |
| 6,354,136 | B1 | 3/2002 | Bremer et al. |

FOREIGN PATENT DOCUMENTS

| EP | 1 118 651 | | 9/2005 |
| WO | WO 2007/006398 | | 1/2007 |
| WO | WO 2008/074511 | | 6/2008 |
| WO | WO 2008074511 | A1 * | 6/2008 |

OTHER PUBLICATIONS

Abad, Carlos et al.,"*Emulsion Copolymerization in Continuous Loop Reactors*", Chemical Engineering Science, vol. 49, No. 24b, pp. 5025-5037, Dec. 31, 1994.
"*Aprobacion Definitiva Del Servicio Municipal De Aguas*", Boletin Oficia De Gipuzkoa, No. 247, 18989, Dec. 28, 1999.

* cited by examiner

*Primary Examiner* — Yong Chu
(74) *Attorney, Agent, or Firm* — Luke A. Parsons; Leandro Arechederra, III

(57) ABSTRACT

The startup of a tubular reactor containing fresh or regenerated molecular sieve catalyst and cooled by steam generation on the shell side, as part of an olefin oligomerization process, is improved by, during the startup phase of the reactor, controlling the pressure on the shell side of the reactor at maximum 10 barg. The startup may be further improved by controlling the inlet temperature of the hydrocarbon startup stream to the reactor, by controlling the flow of reactant olefins to the reactor, or by controlling the nature and/or concentration of the olefins in the reactor feed.

Figure 1:
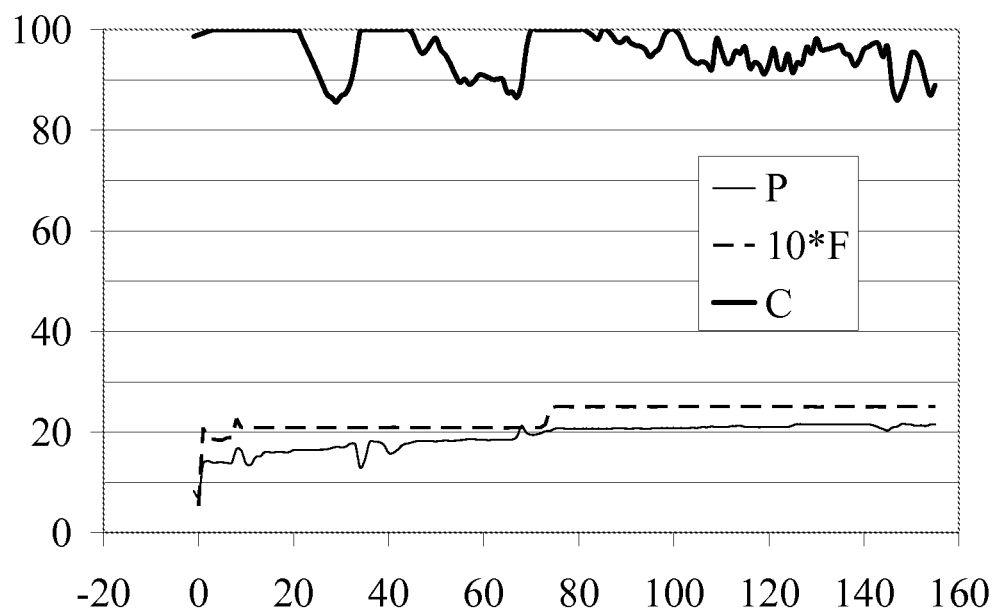

15 Claims, 3 Drawing Sheets

OLIGOMERISATION PROCESS

PRIORITY CLAIM

This application is a National Stage application of International Application No. PCT/EP2010/067989 filed Nov. 23, 2010, which claims the benefit of prior E.P. Patent Application No. 09179262.2 filed Dec. 15, 2009, the disclosures of which are hereby incorporated by reference in their entireties.

FIELD OF THE INVENTION

The present invention relates to improvements in or relating to the oligomerisation of olefins over a molecular sieve or zeolite catalyst in tubular reactors. On an industrial scale it is desirable that oligomerisation reactors can run continuously for as long as possible (i.e. achieve long catalyst life) and that the conversion and selectivity of the reaction is maintained over such extended production runs. The present invention is concerned with improving the startup procedure of the tubular reactor in order to contribute to these objectives.

BACKGROUND OF THE INVENTION

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as propene, 2-methylpropene, 1-butene and 2-butenes, pentenes and hexenes) can be converted by oligomerisation to a product which is comprised of oligomers and which is of value as a high-octane gasoline blending stock and as a starting material for the production of chemical intermediates and end-products. Such chemical intermediates and end-products include alcohols, acids, detergents and esters such as plasticiser esters and synthetic lubricants. Industrial oligomerisation reactions are generally performed in a plurality of tubular or chamber reactors. Solid phosphoric acid, ion exchange resins, liquid phosphoric acid, sulphuric acid, molecular sieves, and zeolites, are known catalysts for oligomerisation.

Zeolites and other molecular sieves have become useful as catalysts for the oligomerisation of olefins. Zeolite oligomerisation processes have been disclosed in a number of documents too high to allow their reference in this document.

Industrial hydrocarbon conversion processes employing zeolite catalysts typically run for several weeks or months before a catalyst change is required or a decommissioning of the reactor is needed. There is a general desire to increase run length to increase catalyst use and to reduce the amount of down time. However it is necessary to balance increasing the run length with the production of the desired product. Various attempts have been made to accomplish this, such as by the development of new catalysts or the control of temperature and pressure in the reactors, as described in WO 2007/006398, and/or the space velocity, as described in WO 2008/074511.

The molecular sieves, typically in their acid form, have been replacing solid phosphoric acid (sPA) catalysts that have been the oligomerisation catalysts of choice for over half a century, since their introduction in the 1930's. Molecular sieves have particularly been successful in replacing solid phosphoric acid catalysts used for oligomerisation in tubular reactors. We have now found that the conventional procedure for starting up a tubular reactor, as it was used on solid phosphoric acid catalyst, leads to problems with zeolite oligomerisation catalysts.

Tubular oligomerisation reactors are designed like a shell and tube heat exchanger and are typically mounted with the tubes in a vertical position. The catalyst is usually located as a fixed bed of catalyst particles inside the tubes of the reactor, and the reactor is cooled with a heat transfer fluid on the shell side. Most conveniently the heat of the reaction is removed by vaporising or boiling up water on the shell side of the reactor. Suitable water for steam generation is a most readily available in a chemical plant, water has a very high heat of vaporisation compared to possible alternatives, and a boiling up regime provides a very high heat transfer rate from the tube wall. For that purpose, the shell side of the reactor is typically connected with a steam drum, from which water for the reactor is obtained as a liquid and into which the mixture of water and boiled up steam, which is generated in the oligomerisation reactor, is returned. The returning steam and water separate inside the steam drum, steam is removed from the steam drum, typically under pressure control, and make-up water is supplied, typically under level control, from a higher pressure source, to maintain an inventory of water in the steam drum. The steam is typically directed into a steam main or header, which operates at a typically constant pressure level and connects the appropriate steam generators with the appropriate steam consumers that are geographically sufficiently close. A chemical plant may comprise several steam mains or headers, which are typically maintained at different pressures. Steam at a higher pressure is typically of a higher value than steam at a lower pressure. Most of its heat content is in the latent heat, i.e. the heat of condensation. The condensation temperature of higher pressure steam is higher than this of lower pressure steam, enabling it to provide heat at a higher temperature level, which is more precious. Steam may be let down from a higher pressure main to a lower pressure level, simply through a control valve, or preferably through a turbine which can at the same time provide mechanical work.

During operation of the oligomerisation reactor, the catalyst typically looses activity over time, and it is customary to compensate for the activity loss by increasing the temperature in the reactor. With tubular reactors, this is conveniently accomplished by raising the pressure in the steam drum, such that the boil up temperature on the shell side of the reactor increases, which then increases the temperature in the catalyst bed located inside the tubes of the reactor. WO 2007/006398 describes how typically a temperature profile with a peak develops along the length of a reactor tube, and teaches to control the height of the peak temperature to no more than 50 degrees C. above the temperature of the temperature control fluid as this fluid exits the reactor, in order to achieve a high reactor runlength. WO 2008/074511 describes how the runlength of a zeolite oligomerisation reactor may be extended by running the reactor with a higher-than-average space velocity early in the run, and reducing the space velocity as the temperature increases further through the run. WO 2008/074511 further describes how the reactor runlength may be further extended by reducing the vulnerability of the reactor operations to unintentional variations in the enthalpy balance as it approaches its end-of-run. These publications are concerned with optimising normal operations for a tubular reactor throughout its run, and extending the length of the run. They are silent about the start up phase of the reactor, i.e. the period of reactor operation before stable early-run conditions are obtained. We have found that the start up method may be improved, such that overall production of desired products and total runlength of a reactor may be increased.

We have found that molecular sieve catalysts, either when fresh or freshly regenerated, are characterised by a surprisingly high activity. This activity is much higher than the activity of fresh sPA catalysts, because sPA catalysts can only reach their maximum activity once the ideal hydration conditions are achieved for the temperature the catalyst operates at, and because there is a high inertia in the hydration mechanisms and their controls. EP 1118651 discloses a process using solid phosphoric acid catalyst using a start-up fluid that is anhydrous, with the purpose to bring the catalyst to its desired hydration conditions sooner.

With fresh zeolite or molecular sieve catalysts, all active sites are inherently active from the start of the contacting with the olefin, and a maximum number of active sites are available when the reactor is started up.

We have found that the conventional start up method for a tubular reactor is not appropriate for a reactor containing fresh zeolite or molecular sieve catalysts. Following the conventional start up method, the reaction is allowed to progress too fast and too far, and produces much heavier oligomers than those that are desired, usually referred to as "heavies", and partially to the formation of even heavier asphalt-like heavy byproducts, also known as "coke". This uncontrolled overshoot leads to a fast coking up of the most active sites on the catalyst, which thus become unavailable for further participation in the oligomerisation reaction even before stable early run conditions have been established. The longer the overshoot lasts, the more damage is caused to the molecular sieve catalyst, and the more undesired heavier oligomers are produced.

There therefore remains a need for an improved start up procedure, whereby stable early run conditions may be reached with a reduced loss of the more active sites on the catalyst, and while more desired oligomer products may be produced instead of heavies. The present invention aims to obviate or at least mitigate the above described problem and/or to provide improvements generally.

SUMMARY OF THE INVENTION

According to the invention, there is provided an improved oligomerisation process as defined in any of the accompanying claims.

In a class of embodiments, the invention therefore provides a process for the oligomerisation of an olefin comprising contacting a hydrocarbon feed stream containing the olefin with a molecular sieve oligomerisation catalyst comprised in the tubes of a tubular reactor in which water is vaporized on the shell side, wherein, during the startup phase of the reactor, after loading fresh or regenerated molecular sieve catalyst into the reactor tubes, after pressurizing the tube side of the reactor with a hydrocarbon startup stream and starting hydrocarbon flow through the tube side, before the target per pass conversion of the olefin and the target space velocity and olefin concentration in the hydrocarbon feed stream to the reactor for normal operation under early run conditions are reached and controllable in a stable manner, the pressure on the shell side of the reactor is controlled at maximum 10 barg, preferably at most 7 barg, preferably in the range of from 3 to 6 barg.

The process according to several embodiments of the invention increases the cooling capacity at the shell side of the tubular reactor. As heat generation during the start up phase may be locally much higher than during normal operation, this maximises the possibility for heat removal from the catalyst bed at those locations and minimizes any possible reaction and temperature overshoot, both in size and in time. With the tighter control provided by the present invention, the per pass conversion of the feed olefin or olefins is more quickly brought down to the desired level, such as at most 98%, more preferably at most 95% and even more preferably at most 90%, and normal operations under stable early-run conditions may be reached in a minimum of time, with during the start up period a minimum loss of catalyst activity and a minimum loss of valuable feed molecules into undesired heavy oligomers. We prefer to bring the per pass conversion of the feed olefin or olefins as soon as possible down to the target for normal operation under early run conditions, which is one of the elements defining the end of the startup phase of the reactor. This minimizes the time during which reaction and temperature may overshoot, and thus the negative effects thereof. The effect of the operating strategy during the startup phase of the reactor is that the catalyst becomes "conditioned", or in other words that "the edge" of the extremely high activity is removed off the catalyst, in as short a time as possible and while minimising any productivity debits and any loss of catalyst activity which would otherwise shorten the overall runlength of a newly loaded reactor.

DETAILED DESCRIPTION

The current invention is concerned with operations during the startup phase of a tubular reactor containing a molecular sieve oligomerisation catalyst. After loading fresh or regenerated catalyst into the reactor, the reactor is typically closed and the air inside the reactor is typically replaced by an inert gas, such as nitrogen. Boiler feed water is typically introduced into the shell side of the reactor, and we prefer to heat up the reactor by introducing also steam into the reactor shell side. Subsequently or in parallel, a hydrocarbon startup stream is usually introduced on the tube side, i.e. the process side of the reactor. When olefin is introduced into catalyst bed, the oligomerisation reaction starts and releases heat towards the shell side of the reactor.

Conveniently, the heat released by the oligomerisation reaction is put to an economic use, and in one embodiment of the present invention therefore the steam generated at the shell side of the reactor during the start up phase is directed into a low pressure steam header or main, such that the steam may be directed to a suitable consumer. Even if a suitable steam consumer is not available or connected to the low pressure steam header or main, excess steam from the header may still be condensed such that at least the condensate may be recovered and recycled to one of the steam generators on site. This reduces the overall consumption of water with the quality required for steam generation. Depending on conditions such as the nature and reactivity of the feed olefin, the concentration of the olefin in the hydrocarbon startup stream, the desired flow of the startup stream, and/or when there is no suitable low pressure steam header or main available, the steam generated from the reactor during the startup phase may alternatively in another embodiment of the present invention be vented to atmosphere. This brings the advantage that the pressure on the shell side of the reactor may be minimised, such as to 1 barg or even lower, only limited by the pressure drop over the pressure control system to atmosphere. This maximises the cooling capacity at the reactor shell side without having to resort to even lower pressures which would require pulling vacuum and for which process complexity significantly increases. When the steam is vented to atmosphere, the condensate is typically not recovered.

The hydrocarbon startup stream is typically a liquid under the operating pressure of the oligomerisation process. We prefer to operate the tubular reactor at a pressure at the process side whereat the process streams are either liquid or in dense phase, also at the highest occurring operating temperatures, and the occurrence of vapour or mixed phases is avoided.

We have found that when vapour or mixed phases are avoided, and the reacting mixture remains a liquid or a dense phase, heat generated by the reaction can move more readily away from the point of generation on the catalyst, into the bulk of the reacting mixture and further to the wall of the reactor tubes. We therefore prefer to operate the tubular reactor with an outlet pressure that is at least 50 barg, more preferably at least 55 barg, even more preferably at least 60 barg, yet more preferably at least 65 barg, and typically as high as 70 barg or even 80 barg. This brings the advantage of a faster diffusion of the heat from the active sites on the catalyst where it is generated to the heat sink on the shell side of the reactor. This faster heat diffusion reduces damage to the catalyst active sites which may be caused by excessive local temperature excursions. We have found that the dense phase and the liquid phase also provide for a better diffusion of the oligomer produced by the reaction from the active site on the catalyst into the bulk of the reaction mixture. This reduces the opportunity for the oligomer to further react and form heavier oligomers which are typically less desired. Also the chance for cracking and other side reactions is thereby reduced, including the reactions that lead to the asphalt-like tar and coke, which have the tendency to remain on the catalyst and cause deactivation.

In an embodiment of the present invention, the tubular reactor is preheated, and preferably to a temperature that is above the temperature at which the water vaporises on the shell side of the reactor. We conveniently use a preheat temperature that is above the saturation temperature at which the water vaporizes on the shell side of the reactor at the start-up condition steam drum pressure, preferably the preheat temperature being at least 5 degrees C., preferably in the range of from 5 to 35 degrees C., more preferably in the range of from 5 to 20 degrees C. above the saturation temperature at which the water vaporizes on the shell side of the reactor at the start-up condition steam drum pressure. This brings the advantage that steam generation at the shell side may start, and steam drum pressure may already come into control, even before any substantial amount of olefin has reached the oligomerisation catalyst and/or the reaction has started. The pressure control system when already operating in control mode is much more responsive than when it is not. The advantage is that when the reaction starts and steam generation increases significantly as a result thereof, the pressure control system reacts more quickly and possible reaction and temperature overshoots may be further reduced.

Several methods are suitable for preheating the tubular reactor. One suitable method is by introducing preheated boiler feed water (BFW) and/or steam into the reactor shellside.

This method of preheating is conveniently practised before starting hydrocarbon flow through the process or tube side of the reactor. It has the advantage that it requires minimal extra equipment and thus incurs little extra investment cost. Another suitable method is by preheating the hydrocarbon startup stream to the reactor to a suitable temperature.

Particularly when the composition of the startup stream is different from the composition of the regular reactor feed stream, but also when the desired preheat temperature is different from the preheat temperature of the regular reactor feed which is passed on to other oligomerisation reactors operating in parallel with the reactor in startup phase, this method requires a separate feed preheat system for the reactor in startup phase, and hence requires extra equipment and investment. The advantage of this preheat method is that it allows a tighter temperature control of the reactor during its startup phase.

The optimal reactor preheat temperature typically depends on the influx of reactive olefins that are fed to the reactor in the startup phase, which is in direct proportion with the expected rate of heat generation in the reactor. If the hydrocarbon startup stream to the reactor is relatively rich in reactive olefins, such as when it is the same as, or has a composition similar to, regular reactor feed, then it is further dependent on the reactivity of the reactive olefins. If these olefins are propylene and/or isobutylene, we conveniently use a preheat temperature for the reactor feed during the startup phase that is in the range of 80-160° C. If these olefins are normal butenes, such as n-butene-1, cis-butene-2 and/or trans-butene-2, we conveniently use 100-180° C., preferably at least 120° C. If the hydrocarbon startup stream to the reactor is diluted, such as containing at most 40% by weight of reactive olefins, as described hereinbelow, we conveniently use a preheat temperature of the feed to the reactor during the startup phase in the range of 140-180° C., preferably from 150° C. to 170° C.

In one embodiment of the process according to the present invention, the hydrocarbon startup stream comprises a portion of the hydrocarbon feed stream containing the olefin and wherein the flow through the reactor tube side is gradually increased up to the target space velocity for normal operation under early run conditions. The gradual flow increase is preferably performed stepwise. The flow increase may be performed manually in 3 or 4 steps, or may more preferably be performed in many small steps, such as by a ramping up procedure that may be computer controlled. With olefin present, oligomerisation may already start as soon as the startup stream is introduced into the reactor at a temperature that is sufficient for the reaction to occur. The gradual increase of flow of the startup stream containing the olefin gradually increases the flow of reactants to the reactor, and thus also the rate at which heat may be generated in the reactor, and the flow is preferably controlled in such a manner that the heat removal system remains able to cope with the gradually increasing heat that is generated. The flow through the reactor tube side is preferably increased up to the target space velocity for normal operation under early run conditions, one of the elements defining the end of the startup phase of the reactor.

In addition to controlling the flow of reactants to the reactor, also the feed inlet temperature may be adjusted to further assist in controlling the overall enthalpy balance over the reactor during the startup phase. We prefer however to keep the feed inlet temperature above 20 degrees C. below the temperature at which the steam is generated at the shell side of the reactor. We prefer that the feed inlet temperature does not drop lower because the catalyst located at the inlet of the tubes would not become sufficiently active for loosing its propensity for reaction overshoot, and would not loose "its edge" of activity. A further disadvantage would be that the heat generation would concentrate over a shorter part of the tube, which would then lead to a higher peak temperature. An advantage of using an inlet temperature below the steam generation temperature is that part of the heat generated by the reaction is absorbed in further feed preheat, such that less overall steam is generated, and the pressure control on the steam outlet from the steam drum may be easier.

In an embodiment of the present invention, the hydrocarbon startup stream comprises a stream that is recycled from the reactor outlet or from a fractionation section downstream of the oligomerisation reaction, or a stream that is obtained from an external source. In this embodiment, the hydrocarbon startup stream preferably is less reactive than the hydrocarbon feed stream containing the olefin. We prefer to use as a component of the hydrocarbon startup stream a stream that is less reactive but that is not foreign to the oligomerisation process, and/or which is readily acceptable to the process. Suitable streams are a recycle from the reactor outlet or a recycle from a fractionation section downstream of the oligomerisation reaction. The latter for instance may be a portion of the light byproduct stream in which saturates, which are typically coming in with the feed, are separated from the reactor effluent and are concentrated. This mostly saturate containing light byproduct stream typically finds an outlet into a larger pool of saturate hydrocarbons, such as a Liquid Petroleum Gas (LPG) pool, a commercial propane pool or a commercial butane pool, together with similar streams originating from other sources at the same location. These recycle streams may thus optionally contain oligomers, which are much less reactive than feed olefin, and/or they may contain saturates, which are inert to the oligomerisation reaction. We prefer to use reactor effluent, recycled from the reactor outlet, preferably after some degree of cooling, because that stream is already at a pressure that is close to the reaction pressure, and only a lower cost booster pump may be sufficient to bring the recycle stream up to sufficient pressure for the recycle. The reactor effluent typically also has a higher density than a stream having a lower average molecular weight, which improves the diffusion inside the reactor, in particular of oligomers produced away from the active site of the catalyst, and hence reduces coking rate. This preferment is particularly suitable for a process comprising several oligomerisation reactors in parallel, and even more suitable for a process in which the target per pass conversion of the feed olefin or olefins is high, such as at least 95% or even at least 97%, because the recycle stream is then even less reactive. A suitable stream may also be obtained from an external source. Preferred streams from such external sources are streams that have a quality similar to the mostly saturate containing light byproduct stream from the oligomerisation process itself and which during normal operation would end up in the same larger pool outlet. Suitable examples are commercial grade propane and/or butane, for instance from a crude pipestill on the same site.

Particularly during the initial startup phase of the tubular reactor, we prefer to limit the concentration of reactive olefins in the feed to the reactor. The invention therefore further provides a process wherein, during the initial startup phase of the reactor, the total concentration of propylene, butene and pentenes in the hydrocarbon startup stream to the reactor is at most 40% by weight, preferably at most 25% by weight, more preferably at most 15% by weight and most preferably at most 10% by weight, based on the total of hydrocarbons in the feed stream. This brings the advantage that the flow of reactants to the reactor containing the highly active catalyst is limited, thereby limiting the amount of heat that may be generated in the reactor. A further advantage is that the reactive olefins are more diluted as compared to normal reactor feed. This reduces the rate of reaction and thus also the rate of heat generation. In addition, the higher amount of diluent provides a matrix for washing the oligomers produced from the catalyst before they are able to react further to undesired heavies or to coke.

During the initial startup phase of the reactor, we conveniently have the total concentration of propylene, butene and pentenes in the hydrocarbon startup stream to the reactor being at least 5% by weight. This feature avoids an unproductive period of time during which no reactive olefins would be fed to the reactor and allows the reaction to kick off sooner.

The reactor may thus be started up with a limited concentration of reactive olefins in the hydrocarbon startup stream. In one embodiment, during the startup phase of the reactor, the total flow of propylene, butene and pentenes in the hydrocarbon flow to the reactor is increased, preferably by introducing more of the hydrocarbon feed stream containing the olefin into the reactor and optionally by reducing the flow rate of the liquid hydrocarbon startup stream, preferably until the flow of the liquid hydrocarbon startup stream to the reactor is stopped. This process feature is preferably performed gradually, it introduces a further control of the influx of reactants to the reactor, and thus of the heat generation rate, and allows to bring the reactor up to using target olefin concentration for normal operation under early run conditions, one of the elements defining the end of the startup phase of the reactor. We have demonstrated that in this embodiment, the temperature profile in the reactor may be flattened out and the occurrence of a temperature peak during startup may be substantially avoided. The disadvantage of this process embodiment is that its investment cost is relatively high, because of separate high pressure pumps for the startup stream, optionally also its separate preheater, and the associated control systems.

We have found that the reactor may also be started up on normal feed. We have found that this may be possible when the normal feed is not overly reactive, such as when the feed concentration of the more reactive olefins, in particular propylene and isobutylene, is not excessive. When starting up on such normal feed, we have found that the space velocity preferably is kept limited for an initial amount of time, more preferably it is controlled according to a particular profile. In one embodiment of the process of the present invention, hydrocarbon feed stream containing the olefin is used as the hydrocarbon startup stream, whereby propylene or isobutylene represent at most 50% by weight of the sum of propylene, butenes and pentenes in the hydrocarbon feed stream containing the olefin, and whereby the space velocity through the reactor tube side is for at least 6 hours kept below 50% of the average space velocity over the full reactor run, optionally followed by keeping the space velocity in the range of 50 to 120% of the average over the full reactor run during at least 48 hours, and optionally further followed by raising the space velocity to above 120% of the average over the full reactor run. The major advantage of starting the reactor up on normal feed is that facilities to provide a diluent for the hydrocarbon startup stream don't have to be provided. We have demonstrated successful reactor startups on feeds that contained 50-70% by weight of total olefins, mostly n-butenes, which contained less than 5% by weight of isobutylene and less than 10% of propylene. We have found that under such conditions a temperature profile having a distinct peak typically cannot be avoided, but that the temperature excursions may remain acceptable. We have also demonstrated successful reactor startups on feeds that contained at most 50% propylene, but we have found that tight control of the steam drum pressure and preferably also of the reactor space velocity become more important under such circumstances.

In some embodiments of the invention, the total flow of reactive olefins to the reactor, more particularly the total flow of propylene, butene and pentenes, is reduced during the startup phase as compared to normal operations. Such processes also carefully administer the total flow of reactants to the reactor such that the heat removal system, which capabilities are increased by embodiments of the present invention, is able to cope with the heat that needs to be removed. When the reaction has started and the first extreme activity, i.e. "the edge" of activity, has been carefully been taken off the molecular sieve catalyst, in particular in the zone at the inlet of the reactor, we prefer to gradually increase the total flow of reactive olefins to the reactor, particularly of propylene, butene and pentenes. The purpose is to keep the period wherein the feed is diluted to a minimum, and move into early run conditions as soon as possible. We have found it useful to monitor the per pass conversion of the reactive olefins as guidance during these operational changes. The total flow of reactive olefins may for instance be increased once small amounts of reactive olefins are noticed in an analysis of the reactor effluent. The risk for reaction and temperature overshoots on the catalyst has thereby reduced, and the operating temperature may be raised. This is preferably achieved by increasing the pressure on the shell side of the reactor. This method of operation allows to control the per pass conversion of the reactive olefins within a preferred range, which is at least 75%, preferably at least 80%, and more preferably at least 85%. Typically, there are steam headers or mains available on site operating at pressures that are higher than the pressure at which the steam is generated during the initial startup phase of the reactor. As soon as the pressure on the shell side of the reactor has reached a level that is above the pressure in a higher pressure steam header or main, we prefer to redirect the steam generated at the shell side of the reactor that is being started up into the higher pressure steam header or main. This brings the advantage that, as soon as it is possible, the heat generated in the reactor may be put to a higher value economic use, and the rate of alternative generation of the higher pressure steam may be reduced.

We have found that the occurrence of reaction and temperature overshoots during the startup phase of a tubular reactor containing molecular sieve oligomerisation catalyst is more difficult to avoid or control with feeds containing an olefin having a higher reactivity.

In an embodiment of the process of the invention, the olefin to be oligomerised during the reactor startup is at least partly replaced after the reactor startup with an olefin having a higher reactivity. The reactor containing the fresh or regenerated catalyst may thus be started up on an olefin that is less reactive than the olefin having the higher reactivity which may be processed during the actual reactor run. This brings the advantage that the reaction is easier to control during the startup phase of the reactor, leading to less or lower temperature overshoots, meaning less activity loss, during the startup phase, and which also may transit into normal run conditions earlier. A suitable example of this embodiment is a reactor which is intended for the oligomerisation of propylene, but which is fed during its startup phase with a feed containing at least one normal butene, more preferably a mixture of normal butenes, and to which propylene feed is only introduced at the earliest when the end of the startup phase is approached, but preferably not before the end of the startup phase is reached. An almost identical example is a reactor which is intended for the oligomerisation of isobutylene. The startup feed does not necessarily be free of the more reactive olefin, but its concentration preferably is low, such as not more than 20% by weight based on the total reactive olefin content, preferably not more than 10% by weight and more preferably not more than 5% by weight on the same basis. Similarly, a reactor intended for the oligomerisation of a feedstock containing at least one higher reactivity olefin selected from propylene, isobutylene or at least one normal butene may be started up according to several embodiments of the present invention on a feed that primarily contains at least one pentene, and which later may be replaced by the feedstock the reactor was intended for. This startup method is particularly suitable for oligomerisation plants having parallel oligomerisation processes in which the feedstocks differ, such as in a plant where propylene is oligomerised in one process to primarily nonenes and/or tetramer, in parallel with a second process to oligomerise butenes, preferably n-butenes, to octenes, optionally a mixture of n-butenes and pentenes to primarily octenes and nonenes, and possibly also decenes. The method is particularly convenient when the reaction products of the different oligomerisation processes are fractionated into the desired oligomer products in common distillation towers.

In another embodiment of the present invention, at least one more reactor is operating in parallel with the tubular reactor that is started up, wherein the hydrocarbon startup stream is different from the hydrocarbon feed stream containing the olefin, and wherein the hydrocarbon startup stream is only fed to the tubular reactor that is started up.

The advantage is that the composition of the feed to the tubular reactor in startup phase, and preferably also its temperature after the feed preheat, may be controlled independently of the operations in the parallel reactor or reactors. In the case that a recycle of reactor effluent is used as at least a portion of the hydrocarbon startup stream, we prefer to use the combined reactor effluent of the two or more reactors that are operating in parallel, as this is more readily available from always the same location in the process, and of which the composition is more stable.

In an embodiment of the process according to the invention, stream compositions are being monitored. In such a process, (i) the conversion per pass over the tubular reactor that is started up is monitored by analysis of the reactor effluent and if needed also by analysis of the reactor feed, preferably by gas chromatography (GC), or (ii) the carbon number distribution of the oligomer produced by the tubular reactor that is started up is monitored by a reactor effluent analysis, preferably by hydrogenation gas chromatography (HGC), more preferably by a gas chromatography apparatus having the hydrogenation step downstream of the sample splitter, whereby, if both conversion per pass and carbon number distribution are monitored by gas chromatography, both analyses are preferably performed in combination on the same sample, using an apparatus comprising one single injection port connected via one or more sample splitters to the GC and the HGC columns.

We have found that monitoring the conversion per pass over the reactor during its startup phase by an analysis of the reactor effluent, and if needed also by an analysis of the reactor feed, is a convenient tool for monitoring when the conversion over the reactor can be taken into control. It helps to understand when a reaction overshoot is occurring and when the reactor returns into control, and this is an important tool in guiding the startup procedure in terms of setting and changing the shell side pressure, and where available also the other operating parameters such as space velocity, concentration and nature of olefin in the feed, operating pressure, the addition of small amounts of catalyst activity moderators such as water, and reactor hydrocarbon feed inlet temperature. Ongoing conversion monitoring also helps in reaching early run conditions as soon as possible, because the target conversion per pass of the olefin may be reached in a minimum of time, and the negative effects of excessive deviations from the target conversion during the startup phase may be minimised. We prefer to do the monitoring of the conversion per pass by gas chromatography (GC), and because the concentration of the reactant olefin or olefins needs to be determined, we prefer to use gas chromatography, without any hydrogenation upstream of the GC column. The analysis of the reactor effluent may be performed off-line, but we prefer to perform this at-line, i.e. in an off-line GC apparatus located close to the sample point in order to reduce the response time.

Even more preferably, we perform the analysis using an on-line GC analyser, which may return the result in an even shorter time, down to at most 5-20 minutes. When the reactor is started up on a regular feed, of which the composition is stable and relatively well known, there is no need to also analyse the feed to the reactor in order to monitor the conversion per pass. When a hydrocarbon startup stream is employed which is different from a regular feed stream during at least part of the startup phase, we prefer to also analyse the composition of the feed to the reactor being started up, for determining the concentration of the reactant olefin or olefins, allowing a closer control of the conversion per pass.

We have found that reactor-by-reactor conversion control is preferably also performed during normal operations, as it allows optimising the operations within the operational boundaries of the process.

Independently, but preferably in combination with the per pass conversion monitoring, we also prefer to monitor the carbon number distribution of the oligomer produced by the tubular reactor that is started up, by a reactor effluent analysis. Excessive selectivities towards heavier oligomers may be another indication of a reaction overshoot, and produces products that are typically less desired. Having a per pass conversion on target, but an undesirable carbon number distribution, is typically a signal that the reactor operations may be further optimised, and may thus trigger an intervention on one of the operating parameters of the reactor discussed before. The carbon number distribution is more conveniently determined using a hydrogenation gas chromatography (HGC), in which olefins in the sample to be analysed are first hydrogenated to the corresponding paraffins before the sample passes through the GC column. This very much simplifies the GC spectrum because it significantly reduces the number of possible isomers. The peaks in a spectrum of a hydro-GC (HGC) can be more easily assigned to a particular carbon number as compared to without hydrogenation, and the carbon number distribution of a complex stream such as the reactor effluent is easier to obtain and becomes more accurate. There is thus no loss of valuable information for the oligomerisation process, due to the hydrogenation step in the GC analysis.

Due to the simpler GC spectrum, it may become possible to assign also isomeric alkane structures to the individual peaks, at least for the oligomers having a C6-C8 carbon number and usually up to including the C9 range, and this may be of value for further processing of the oligomers, such as during cobalt hydroformylation, in which the location of the olefinic double bond may be less important than e.g. the degree of branchiness of the olefinic substance to be reacted, which may influence the reactivity in hydroformylation. There is thus a possibility to increase the amount of valuable information thanks to the hydrogenation step in the GC analysis.

It is our preference to monitor for both the conversion per pass and the carbon number distribution of the oligomer produced by the reactor that is started up. This provides more complete information about the reaction occurring in the reactor being started up. We prefer to perform both monitoring by employing gas chromatography. We have found that it is more convenient to perform the two analyses in combination on the same sample, and we prefer to use an apparatus comprising one single injection port connected via one or more sample splitters to the GC and the HGC columns. This analysis method provides maximum information with a minimum of equipment and minimum of operator assistance, in a minimum of time, in particular when the apparatus is connected on-line with the process.

In a conventional HGC apparatus, it is customary to perform the hydrogenation upstream of where the small amount of sample is split off that is actually directed into the GC column for separation. A typical splitting ratio may be 200:1, meaning that 200 times more material is hydrogenated than what is actually directed into the GC column. The excess material is usually discarded. The analysis is typically performed with hydrogen as the carrier gas. A hydrogenation catalyst, usually a Pt catalyst, is typically packed in the injection port liner, and the entire injected sample is hydrogenated. Oligomerisation reactor effluents may however contain poisons for the hydrogenation catalyst, such as sulphur species. Over time, the hydrogenation step in the GC apparatus may loose its effectiveness, leading to breakthrough of alkenes to the GC column which may invalidate the analysis results. The hydrogenation catalyst in the GC apparatus may thus need regular replacement, during which intervention the apparatus is out of service, and which may be resource demanding. The other drawback of the conventional HGC technique is that the temperature of the hydrogenation step is substantially the same as the temperature of the injection port, and which is typically controlled for a different purpose. There is thus little or no possibility to control the hydrogenation temperature independently, which may lead to excessive temperatures leading to side-reactions such as cracking/demethylation which may distort the analytical result.

We have now found that it is more convenient to relocate the hydrogenation step to downstream of the splitter, and preferably using independent temperature control such as with separate heating blocks. In addition we prefer to provide at least two sample hydrogenators with their respective heating blocks in parallel, and with a valve arrangement allowing a switch from one hydrogenator in service to its counterpart in stand-by. The hydrogenator removed from service may then be replaced or serviced and this is possible without having to take the entire GC apparatus down. An additional advantage is that the hydrogenation catalyst is now only contacted with a small fraction of what the same catalyst in conventional apparatus encounters. The amount of catalyst poisons reaching the catalyst is reduced accordingly. We have found that this may significantly increase the catalyst life of the GC hydrogenator. In conventional GC apparatus, we used to need catalyst replacement every 2 months. After the relocation of the GC hydrogenator to downstream of the sample splitter, we have not needed to replace the catalyst after 24 months of continued operation of the apparatus.

The "molecular sieve catalyst" as used herein may be any molecular sieve that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2) or zeolites of the MTT structure type (for example H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites with the EUO structure type (for example, EU-1), or zeolites of the MFS structure (such as H-ZSM-57), or zeolites of the MWW structure (such as MCM-22 or ITQ-1 or MCM-49), or H-ZSM-48, or any member of the ferrierite structure family (such as ZSM-35). Other examples of suitable catalysts are offretites, H-ZSM-4 (MAZ structure), H-ZSM-18 (MEI structure) or zeolite Beta.

Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites. The H-form of these molecular sieves are preferred because they are typically more active.

We have found that a zeolite having the MFI structure type, such as H-ZSM-5, and operated at a low space velocity, such as less than 1.5 h-1, may be suitable for producing fuel-type products, but that it is less suitable for producing oligomer intermediates for alcohol manufacturing. We therefore prefer to operate the process of the present invention having an MFI structure type oligomerisation catalyst during normal operation at a space velocity that is at least $1.5\ h^{-1}$, preferably at least $2\ h^{-1}$, more preferably at least $3\ h^{-1}$ and even more preferably at least $5\ h^{-1}$.

Another type of molecular sieve suitable for the process of the invention is SAPO-11, which has unidimensional 10-rings like ZSM-22 and ZSM-23.

Additionally, the catalyst can be a zeolite synthesised without addition of a template, for example, faujasites, zeolite L, mordenites, erionites and chabazites, the structures of which are contained in the 'Atlas of Zeolite Structure Types' by C. Baerlocher, W. M. Meler and D. H. Olson (published by Elsevier on behalf of the Structure Commission of the International Zeolite Association, 5th Revision Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolites catalysts; and zeolite catalysts obtained by the addition of different elements (for example boron, iron and gallium), for example, by impregnation or cation exchange, or by incorporation during the zeolite synthesis.

Mixtures of two or more zeolites e.g. a mixture of ZSM-22 and ZSM-57 or ZSM-22 and ZSM-5 can be used as disclosed in EP0746538 B1. Or alternatively, upon the surface of each zeolite crystal, a layer of another zeolite can be deposited as disclosed in EP0808298 B1.

The zeolite conveniently has a crystallite size up to 5 µm, such as within the range of from 0.05 to 5 µm, for example from 0.05 to 2.0 µm, and typically from 0.1 to 1 µm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming It is also possible to use, as is known in the art, a material in which silicon and aluminium have been replaced in whole or in part by other elements. Silicon may, for example, be replaced by germanium and/or phosphorus; and aluminium more especially by boron, gallium, chromium or iron. Materials containing such replacement lattice elements are also generally termed zeolites, and the term is used in this broader sense in this specification.

The zeolites might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

Other suitable oligomerisation catalysts are disclosed in US 2006/0063955 A1.

A preferred process of the present invention employs as catalyst a zeolite having an MFS structure, as disclosed in US 2004/0006250.

In an embodiment of the present invention, the feed to the reactor may be hydrated in order to moderate the reaction and limit the peak temperature in the tubular reactor, such as disclosed in U.S. Pat. No. 5,672,800. The amount of water in the feed may be controlled as disclosed in WO 2005/058777.

The process of the present invention may also be operated with different oligomerisation catalysts stacked as layers in the fixed bed of the tubular reactor, such as disclosed in WO 2005/118512 but more preferably as disclosed in WO 2005/118513. The process may also operate with more than one reactor in series, such as disclosed in WO 2007/024330.

After the startup phase of the tubular reactor according to the present invention, catalyst rejuvenation techniques may be applied, such as those disclosed in WO 2006/128650 or WO 2006/128649.

In the process of the present invention, a peak temperature may be monitored in the tubular reactor and controlled, such as disclosed in WO 2007/006398.

When the process provides for good control of the peak temperature in the tubular reactor, the process according to the invention may also be operated with little to no water in the feed, such as disclosed in WO 2006/133967.

In some embodiments of the present invention, the hydrocarbon feed stream of the process contains an amount of sulphur or sulphur-containing compounds, and the process may be operated as disclosed in US 2004/220440, US 2005/20865 or US 2005/14630.

The hydrocarbon feed stream containing the olefin, of the process according to the present invention, may contain an organic nitrogen-containing Lewis base, and this may be controlled, such as disclosed in WO 2007/104385.

After the startup phase of the tubular reactor according to several classes of embodiments of the present invention, the process may be further operated with varying space velocities throughout the run, such as disclosed in WO 2008/074511.

The effluent from the tubular reactor of the process of several classes of embodiments of the present invention is typically not ready as such for further use. Typically the reactor effluent is separated into streams having narrower component distributions, usually using conventional distillation techniques. It is customary to separate off a stream containing unreacted feed olefins and paraffins that have come in with the feed, and part of that stream may be recycled to the oligomerisation reactor to increase the overall conversion of the process, or to reduce the olefin content of the remainder of that stream such that it may become suitable for a particular further use.

In an embodiment of the present invention, the product of the olefin oligomerisation is fractionated to produce an olefin oligomer product. The olefin oligomer product may typically have a narrower boiling range as compared to the product of the olefin oligomerisation, which may make it suitable for some of the downstream processes that convert olefin oligomers to further derivatives.

In a further embodiment of the present invention, the olefin oligomer product is subjected to hydroformylation, optionally followed by hydrogenation, to form an alcohol.

The alcohol process strongly prefers to use olefin oligomers having a narrow boiling range, preferably also a narrow carbon number range, primarily because of the separation steps such process comprises. Suitable techniques to convert the olefin oligomer product into a product alcohol are disclosed in too many publications to list. We prefer to use any of the techniques disclosed in WO 2005/58787, WO 2005/

058782, WO 2006/122526, WO 2008/128852, WO 2006/086067 and in copending patent applications PCT/EP2009/005996, PCT/EP2009/005995, PCT/EP2009/066289 and U.S. Ser. No. 61/183,575.

An alcohol produced according to the present invention may find use as an intermediate for a surfactant, such as an ethoxylate, a sulphate or an ethoxy-sulphate, but even more important is its use as an intermediate for an ester. In yet a further embodiment of the present invention, the alcohol is esterified with an acid or an anhydride to form an ester, whereby preferably the acid or acid anhydride is selected from the group consisting of benzoic acid, phthalic acid, adipic acid, trimellitic acid, cyclohexanoic acid, cyclohexanoic dibasic acid, pyromellitic acid and their anhydrides, and mixtures thereof. Esters find many uses, such as in synthetic lubricants but more importantly as plasticisers for polyvinylchloride (PVC), in particular when the alcohol is esterified with at least one of the acids or anhydrides listed above. Suitable techniques to convert the alcohol to the ester are disclosed in too many publications to list. We prefer to use any of the techniques disclosed in WO 2005/021482, WO 2006/125670, WO 2008/110305 and WO 2006/110306.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexanoic equivalents, such as mono-alkyl, di-alkyl or tri-alkyl cyclohexanoates. In particular, di-isononyl phthalate (DINP) may be further hydrogenated to form di-isononyl cyclohexanoate. The process of the invention may therefore be for the production of a phthalate di-ester, in particular DINP, and further comprise the hydrogenation of the phthalate di-ester to the corresponding cyclohexanoate, in particular di-isononyl cyclohexanoate.

Alternatively, a mono-benzoate may be produced, such as isononyl benzoate or isodecyl benzoate, or a mixture thereof, and the mono-benzoate may be hydrogenated to the corresponding cyclohexanoate.

In yet another further embodiment of the present invention therefore, wherein the ester is a phthalate or a benzoate ester, the process further comprises the hydrogenation of the ester to a cyclohexanoate ester. Suitable hydrogenation processes to produce such cyclohexanoates, and catalysts for these processes, are disclosed in EP 5737, EP 1042273, EP 814098, EP 1412082, EP 1899051 or its equivalent CA 2612435, EP 1511582, EP 1549603, US 2004/0260113, US 2006/0149097, US 2006/0166809 and WO 2004/046078. We prefer to use a supported active metal catalyst, preferably having Ru as at least one of the active metals, and more preferably comprising ruthenium on a silica or on a carbon support. More details on the catalyst may be found in copending patent application PCT/EP2009/005996.

The present invention is now further illustrated by means of the following examples.

Example 1

Comparative

The tubes of a tubular reactor were loaded with freshly regenerated acidic zeolite catalyst, whereby in the direction of the process flow a first layer of H-ZSM-22 based catalyst preceded a second layer of H-ZSM-57 based catalyst, and whereby the first layer occupied from 40-52% of the volume of the total catalyst bed, on average about 46%. Boiler feed water was introduced into the steam drum connected to the reactor shell side, and into the shell side of the reactor, and a normal liquid level was established in the steam drum. The reactor was preheated to 200° C. by introducing 20 barg saturated steam into the shell side of the reactor. At time 0 hrs, regular olefin feed with the composition given in Table 1 was introduced into the process side of the reactor.

TABLE 1

| Feed (Wt %) | Typical | Range |
| --- | --- | --- |
| Ethane and Ethylene | 5.70 | 5.00-6.40 |
| Propane | 20.40 | 18.90-22.40 |
| Propylene | 52.58 | 50.50-54.80 |
| Butane + Isobutane | 19.15 | 16.50-21.70 |
| Trans Butene-2 | 0.78 | 0.50-1.10 |
| Cis Butene-2 | 0.66 | 0.50-0.80 |
| Isobutene + Butene-1 | 0.55 | 0.40-0.80 |
| Pentenes | 0.18 | 0.05-0.40 |
| Total | 100.00 | |

The feed was introduced at a rate equivalent to a weight hourly space velocity (WHSV) in the range of 2-3 (tons/ton/hr or $h^{-1}$), which was the target for early run conditions on this feedstock. The target for the per pass conversion was 90%, based on propene in the reactor feed. The steam drum pressure was initially controlled at 13 barg. FIG. 1 shows the steam drum pressure P in barg, the olefin feed weight hourly space velocity 10*F in $10*h^{-1}$, i.e., multiplied by a factor of 10 for a convenient showing in the graph, and the propene per pass conversion measured over the reactor C in %, during the first 160 hrs of operation.

FIG. 1 shows that the conversion was unstable for a long period of time, and only started showing signs of reasonable controllability around 140 hrs of operation.

Example 2

The tubes of a tubular reactor were loaded with freshly regenerated acidic zeolite catalyst of the type H-ZSM-57. Boiler feed water was introduced into the steam drum connected to the reactor shell side, and into the shell side of the reactor, and a normal liquid level was established in the steam drum. The reactor was preheated to 135° C. by introducing 40 barg saturated steam into the shell side of the reactor. At time 0 hours, feed with the composition as given in Table 2 was introduced into the process side of the reactor, and which feed was preheated as stated below.

TABLE 2

| Feed (wt %) | Typical | Range |
| --- | --- | --- |
| Propylene | 0.07 | 0.07-0.10 |
| Butane | 47.05 | 43.61-48.61 |
| n-Butenes (Butene-1, cis and trans Butene-2) | 39.24 | 37.64-44.84 |
| Isobutane | 13.42 | 12.31-13.82 |
| Isobutene | 0.15 | 0.13-0.18 |
| Pentenes | 0.07 | 0.05-0.10 |
| Total | 100.00 | |

Figure 2:
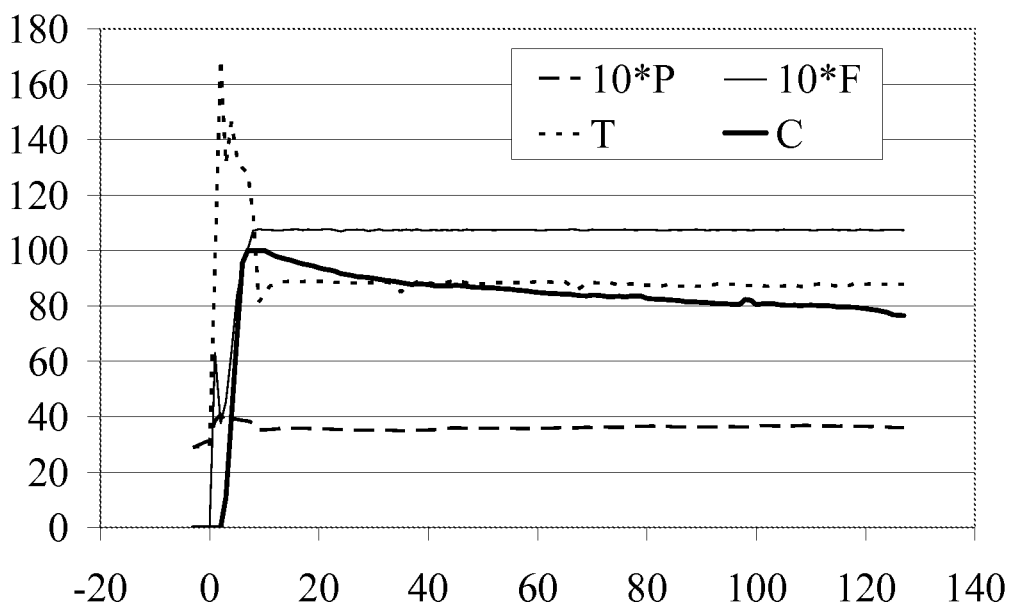

The feed was introduced at a rate equivalent to a weight hourly space velocity (WHSV) in the range of 9-11 (tons/ton/hr or $h^{-1}$), which is the target for early run conditions on this feedstock. The target for the conversion per pass was 75%, based on the amount of butenes in the reactor feed. The steam drum pressure was controlled at 3-4 barg, and the steam was routed to a low pressure steam system. FIG. 2 shows the steam drum pressure P in barg*10, the olefin feed weight hourly space velocity F in $10*h^{-1}$, the feed inlet temperature T in deg C, and the butenes per pass conversion measured over the reactor C in %, during the first 125 hrs of operation. FIG. 2 shows that under these conditions, it took about 120 hrs of operation before the target per pass conversion and the target olefin space velocity and olefin concentration in the reactor feed for normal operation under early run conditions were reached and became controllable in a stable manner.

Example 3

The tubes of a tubular reactor were loaded with freshly regenerated acidic zeolite catalyst, whereby in the direction of the process flow a first layer of H-ZSM-22 based catalyst preceded a second layer of H-ZSM-57 based catalyst, and whereby the first layer occupied from 40-52% of the volume of the total catalyst bed, on average about 46%. Boiler feed water was introduced into the steam drum connected to the reactor shell side, and into the shell side of the reactor, and a normal liquid level was established in the steam drum. The reactor was preheated to 135° C. by introducing saturated 40 barg steam at the shell side of the reactor. At time 0 hours, olefin feed with the composition as given in Table 3 was introduced, and which was preheated to as stated below.

TABLE 3

| Feed (wt %) | Typical | Range |
| --- | --- | --- |
| Propylene | 0.08 | 0.07-0.13 |
| Butane | 42.23 | 41.23-44.23 |
| n-Butenes (Butene-1, cis and trans Butene-2) | 48.26 | 46.76-50.92 |
| Isobutane | 9.15 | 9.0-9.5 |
| Isobutene | 0.18 | 0.17-0.19 |
| Pentenes | 0.10 | 0.08-0.17 |
| Total | 100.00 | |

Figure 3:
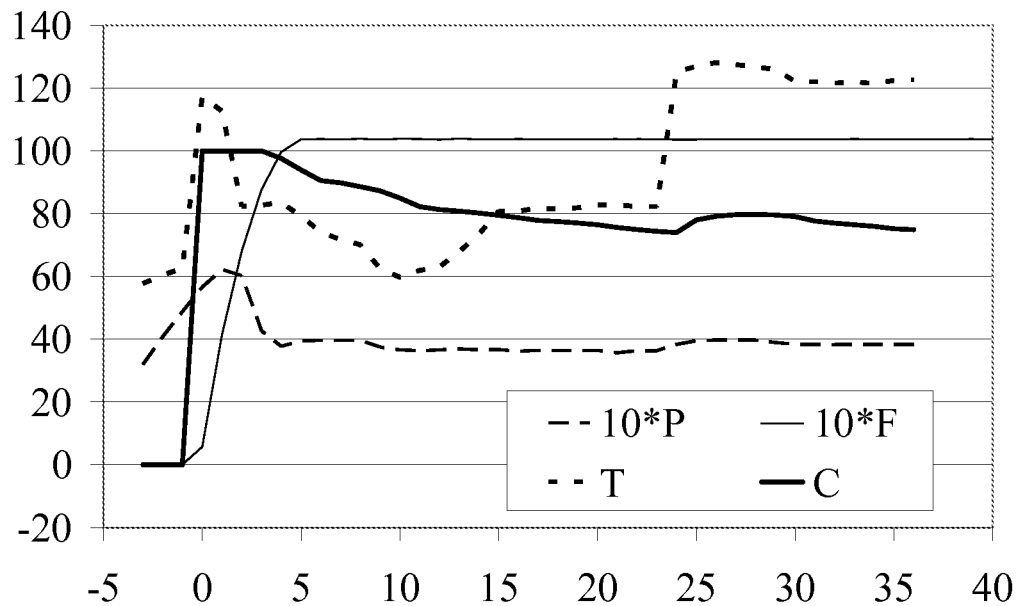

The feed was introduced at a rate equivalent to a weight hourly space velocity (WHSV) in the range of 9-11 (tons/ton/hr or $h^{-1}$), which is the target for early run conditions on this feedstock. The target for the conversion per pass was 75%, based on the amount of butenes in the reactor feed. The steam drum pressure was controlled at 3-4 barg, and the steam was routed to a low pressure steam system. FIG. 3 shows the steam drum pressure $10*P$ in $barg*10$, the olefin feed weight hourly space velocity $10*F$ in $10*h^{-1}$, the feed inlet temperature T in deg C, and the butenes per pass conversion measured over the reactor C in %, during the first 36 hrs of operation. During the first 24 hrs of operation, the feed inlet temperature was kept lower than in normal operation, i.e. below 120° C. and mostly around 80±20° C., and in that time the target conversion of 75% was already reached after 24 hrs.

Subsequently the inlet temperature was raised from about 80° C. to 120-130° C., its level for normal operation during early run conditions. On the now already conditioned catalyst, only a small (5%) conversion increase was experienced as a result of the temperature increase, and the conversion per pass returned to its 75% target after another 12 hrs of operation. FIG. 3 shows that with this startup strategy, it took about 36 hrs of operation before the target per pass conversion and the target olefin space velocity and olefin concentration in the reactor feed for normal operation under early run conditions were reached and became controllable in a stable manner.

Example 4

The tubes of a tubular reactor were loaded with freshly regenerated acidic zeolite catalyst, whereby in the direction of the process flow a first layer of H-ZSM-22 based catalyst preceded a second layer of H-ZSM-57 based catalyst, and whereby the first layer occupied from 40-52% of the volume of the total catalyst bed, on average about 46%. Boiler feed water was introduced into the steam drum connected to the reactor shell side, and into the shell side of the reactor, and a normal liquid level was established in the steam drum. The reactor was preheated to 170° C. by passing during about 5 hrs through the reactor a hot diluent hydrocarbon stream, which contained less than 10 wt % C3 olefin. The composition of the diluent stream is given in Table 5. At time 0 hours, regular olefin feed containing 50-52 wt % propylene was also introduced, at its target weight hourly space velocity of 2-3 $h^{-1}$ for early run conditions. The composition of the regular olefin feed stream is given in Table 4. The diluent stream was continued, and the combined feed to the reactor was containing about 37% wt propylene.

TABLE 4

| Regular Olefin Feed (wt %) | Typical | Range |
| --- | --- | --- |
| Ethane and Ethylene | 2.95 | 2.70-3.40 |
| Propane | 18.93 | 18.60-19.50 |
| Propylene | 58.90 | 58.10-59.60 |
| Butane + Isobutane | 16.90 | 17.60-16.20 |
| Trans Butene-2 | 0.81 | 0.77-1.02 |
| Cis Butene-2 | 0.59 | 0.55-0.62 |
| Isobutene + Butene-1 | 0.87 | 0.74-0.97 |
| Pentenes | 0.05 | 0.01-0.12 |
| Total | 100.00 | |

TABLE 5

| Diluent Stream (wt %) | Typical | Range |
| --- | --- | --- |
| Ethane and Ethylene | 7.80 | 7.70-7.90 |
| Propane | 29.50 | 28.00-33.00 |
| Propylene | 6.50 | 5.50-7.00 |
| Butane + Isobutane | 51.44 | 49.70-52.50 |
| Trans Butene-2 | 2.42 | 2.25-2.65 |
| Cis Butene-2 | 1.45 | 1.35-1.59 |
| Isobutene | 0.23 | 0.16-0.29 |
| Butene-1 | 0.66 | 0.61-0.71 |
| Total | 100.00 | |

Figure 4:
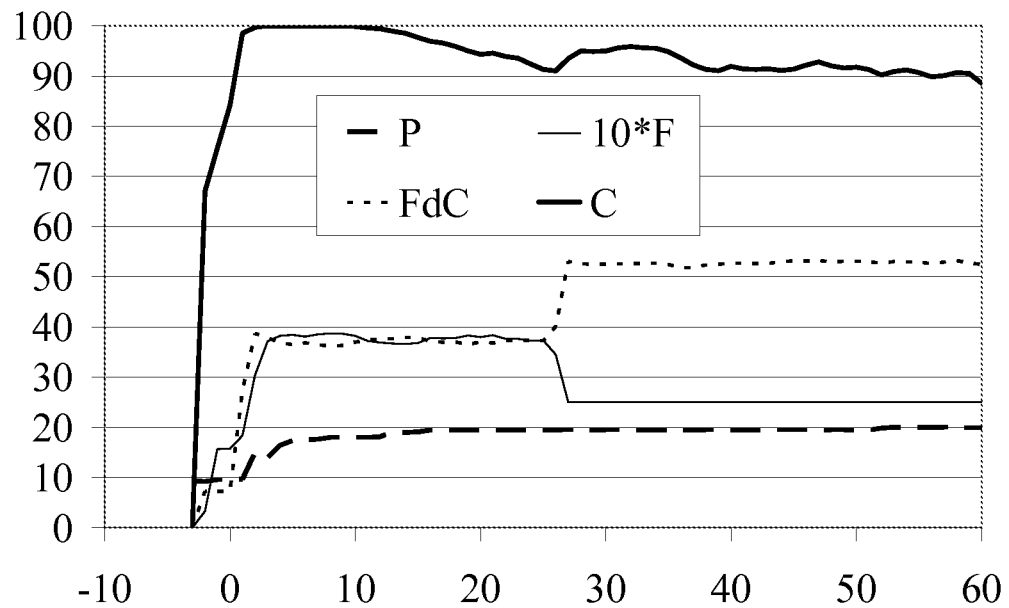

FIG. 4 shows the steam drum pressure P in barg, the olefin feed weight hourly space velocity $10*F$ in $10*h^{-1}$, the feed inlet propylene concentration FdC in wt %, and the propylene per pass conversion measured over the reactor C in %, during the first 60 hrs of operation. As shown in the graph, the target for the conversion per pass of 90% was approached after about 26 hrs of operation, while the steam drum pressure was already allowed to increase from its initial 10 barg to close to 20 barg. Subsequently, the diluent stream was discontinued and only regular feed containing about 52% wt propylene was fed.

On the now conditioned catalyst, this step change in feed propylene concentration only caused a 5% rise in per pass conversion, and it returned to its 90% target after another 12 hrs of operation. FIG. 4 shows that only about 40 hrs were needed before the target per pass conversion and the target olefin space velocity and olefin concentration in the reactor feed for normal operation under early run conditions were reached and became controllable in a stable manner.

Example 5

The tubes of a tubular reactor were loaded with freshly regenerated acidic zeolite catalyst of the type H-ZSM-57.

Boiler feed water was introduced into the steam drum connected to the reactor shell side, and into the shell side of the reactor, and a normal liquid level was established in the steam drum. The reactor was preheated to 180° C. by introducing 20 barg saturated steam at the shell side of the reactor. At time 0 hours, a feed with the composition as given in Table 6 was introduced at a weight hourly space velocity of 2-3 $h^{-1}$.

TABLE 6

| Feed (wt %) | Typical | Range |
|---|---|---|
| Propane | 0.90 | 0.84-1.02 |
| Propylene | 4.31 | 3.90-5.10 |
| Butane + Isobutane | 31.30 | 30.00-32.30 |
| n-Butenes (Butene-1, cis and trans Butene-2) | 61.29 | 60.30-65.00 |
| Isobutene | 2.20 | 1.90-2.20 |
| Total | 100.00 | |

Figure 5:
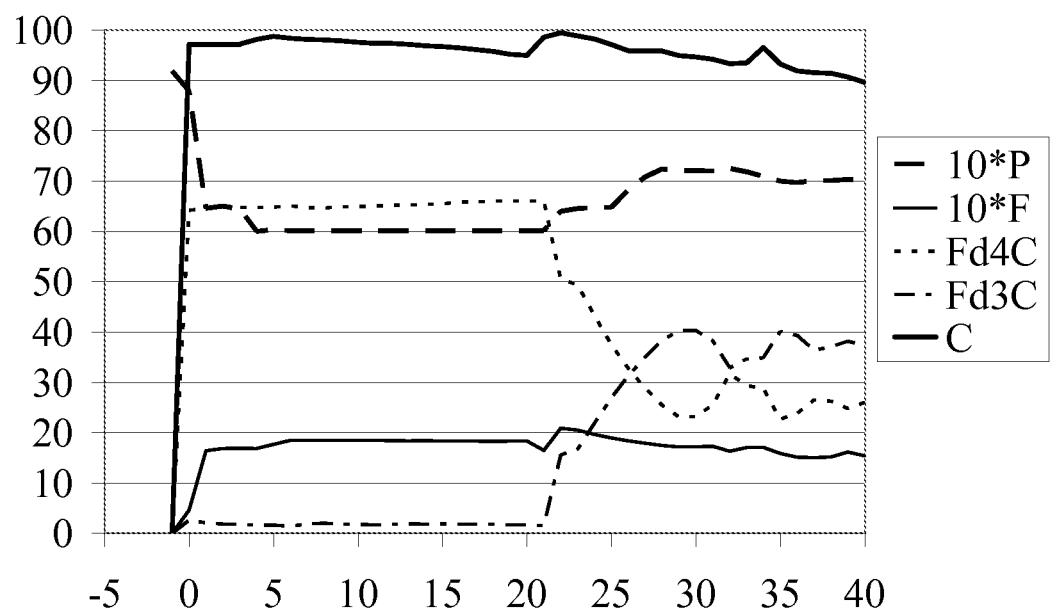

Steam drum pressure was controlled at about 6 barg. FIG. 5 shows the steam drum pressure 10*P in barg*10, the weight hourly space velocity 10*F in 10*$h^{-1}$, the wt % C4 olefin and the wt % propylene in the feed respectively as Fd4Ca and Fd3C, and the olefin per pass conversion measured over the reactor C in %, during the first 40 hrs of operation.

As shown in the graph, the conversion per pass, initially on butene only, started to come down towards 90% after about 20 hrs of operation. At that time, C3 olefin feed was introduced and C4 olefin feed reduced, such that the overall feed olefin concentration was maintained at its target range of 62-66 wt %. After a short and small conversion increase, limited because the catalyst had been properly conditioned during the C4 feed operation, the propylene concentration in the feed could be raised to 35-40 wt % while the target per pass olefin conversion further approached its target of 90%. This C3/C4 mixed feed was the target feedstock for normal operation of this reactor run. FIG. 5 shows that only about 40 hrs were needed before the target per pass conversion and the target olefin space velocity and olefin concentration in the reactor feed for normal operation under early run conditions were reached and became controllable in a stable manner. Based on the experience of Example 4, it is expected that a regular C3 feedstock containing about 52 wt % propylene could be introduced into the reactor conditioned as in this example after about 40 hrs of operation, without causing an excessive increase of olefin conversion.

Having now fully described this invention, it will be appreciated by those skilled in the art that the invention can be performed within a wide range of parameters within what is claimed, without departing from the spirit and scope of the invention. As understood by those of skill in the art, the overall invention, as defined by the claims, encompasses other preferred embodiments not specifically enumerated herein.

The invention claimed is:

1. A process for the oligomerisation of an olefin comprising contacting a hydrocarbon feed stream containing the olefin with a molecular sieve oligomerisation catalyst comprised in the tubes of a tubular reactor in which water is vaporized on the shell side, wherein, during the startup phase of the reactor, after loading fresh or regenerated molecular sieve catalyst into the reactor tubes, after pressurizing the tube side of the reactor with a hydrocarbon startup stream and starting hydrocarbon flow through the tube side, before the target per pass conversion of the olefin and the target space velocity and olefin concentration in the hydrocarbon feed stream to the reactor for normal operation under early run conditions are reached and controllable in a stable manner, the pressure on the shell side of the reactor is controlled at maximum 10 barg.

2. The process according to claim 1, wherein the reactor is preheated to a temperature that is above the saturation temperature at which the water vaporizes on the shell side of the reactor at the start-up condition steam drum pressure.

3. The process according to claim 1, wherein the hydrocarbon startup stream comprises a portion of the hydrocarbon feed stream containing the olefin and wherein the flow through the reactor tube side is gradually increased up to the target space velocity for normal operation under early run conditions stepwise.

4. The process according to claim 1, wherein the hydrocarbon startup stream comprises a stream that is recycled from the reactor outlet or from a fractionation section downstream of the oligomerisation reaction, or a stream that is obtained from an external source.

5. The process according to claim 1, wherein the olefin is selected from the group consisting of propylene, one or more butenes, one or more pentenes, and mixtures thereof, and wherein, during the initial startup phase of the reactor, the total concentration of propylene, butene and pentenes in the hydrocarbon startup stream to the reactor is at most 40% by weight.

6. The process according to claim 1, wherein the olefin is selected from the group consisting of propylene, one or more butenes, one or more pentenes, and mixtures thereof, and wherein, during the startup phase of the reactor, the total flow of propylene, butene and pentenes in the hydrocarbon flow to the reactor is increased by introducing more of the hydrocarbon feed stream containing the olefin into the reactor and by reducing the flow rate of the liquid hydrocarbon startup stream until the flow of the liquid hydrocarbon startup stream to the reactor is stopped.

7. The process according to claim 1, wherein hydrocarbon feed stream containing the olefin is used as the hydrocarbon startup stream, and wherein propylene or isobutylene represent at most 50% by weight of the sum of propylene, butenes and pentenes in the hydrocarbon feed stream containing the olefin, and whereby the space velocity through the reactor tube side is for at least 6 hours kept below 50% of the average space velocity over the full reactor run, followed by keeping the space velocity in the range of 50 to 120% of the average over the full reactor run during at least 48 hours, and further followed by raising the space velocity above 120% of the average over the full reactor run.

8. The process according to claim 6, wherein as the total flow of propylene, butene and pentenes to the reactor increases, also the pressure on the shell side of the reactor is increased.

9. The process according to claim 1, wherein the olefin to be oligomerised during the reactor startup is at least partly replaced after the reactor startup with an olefin having a higher reactivity.

10. The process according to claim 1, wherein at least one more reactor is operating in parallel with the tubular reactor that is started up, wherein the hydrocarbon startup stream is different from the hydrocarbon feed stream containing the olefin, and wherein the hydrocarbon startup stream is only fed to the tubular reactor that is started up.

11. The process according to claim 1, wherein:
the conversion per pass over the tubular reactor that is started up is monitored by analysis of a reactor effluent sample by gas chromatography (GC), and
the carbon number distribution of the oligomer produced by the tubular reactor that is started up is monitored by a reactor effluent sample analysis by hydrogenation gas chromatography (HGC) wherein a hydrogenation step of the analysis is downstream of a sample splitter, whereby, both analyses are performed in combination on the same sample, using an apparatus comprising one single injection port connected via one or more sample splitters to GC and HGC columns.

12. The process according to claim 1, wherein the product of the olefin oligomerisation is fractionated to produce an olefin oligomer product.

13. The process according to claim 12, wherein the olefin oligomer product is subjected to hydroformylation followed by hydrogenation to form an alcohol.

14. The process according to claim 13, wherein the alcohol is esterified with an acid or an anhydride to form an ester, whereby the acid or acid anhydride is selected from the group consisting of benzoic acid, phthalic acid, adipic acid, trimellitic acid, cyclohexanoic acid, cyclohexanoic dibasic acid, pyromellitic acid and their anhydrides, and mixtures thereof.

15. The process according to claim 14, wherein the ester is a phthalate or a benzoate ester and further comprising the hydrogenation of the ester to a cyclohexanoate ester.

* * * * *